United States Patent
Uematsu et al.

(10) Patent No.: US 7,860,354 B2
(45) Date of Patent: Dec. 28, 2010

(54) OPTICAL SENSOR

(75) Inventors: Ikuo Uematsu, Yokohama (JP);
Tomohiro Takase, Sagamihara (JP);
Ichiro Tono, Yokohama (JP); Shingo Kasai, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/265,991

(22) Filed: Nov. 6, 2008

(65) Prior Publication Data

US 2009/0116783 A1 May 7, 2009

(30) Foreign Application Priority Data

Nov. 6, 2007 (JP) ............................ P2007-289082
Oct. 22, 2008 (JP) ............................ P2008-272205

(51) Int. Cl.
*G02B 6/00* (2006.01)
*G02B 6/34* (2006.01)
*G01J 3/00* (2006.01)
*G01N 33/28* (2006.01)

(52) U.S. Cl. .......................... 385/12; 385/37; 356/39; 356/305

(58) Field of Classification Search .................. None
See application file for complete search history.

(56) References Cited

U.S. PATENT DOCUMENTS

| 6,903,815 | B2* | 6/2005 | Uchiyama et al. | 356/305 |
| 7,269,308 | B2* | 9/2007 | Tono et al. | 385/12 |
| 7,410,614 | B2* | 8/2008 | Uchiyama et al. | 422/82.11 |
| 2001/0001021 | A1* | 5/2001 | Kraus et al. | 385/12 |
| 2005/0147342 | A1* | 7/2005 | Uchiyama et al. | 385/12 |
| 2007/0116401 | A1* | 5/2007 | Xia et al. | 385/12 |

FOREIGN PATENT DOCUMENTS

JP          2004-212188           7/2004

* cited by examiner

*Primary Examiner*—Tina M Wong
(74) *Attorney, Agent, or Firm*—Oblon, Spivak, McClelland, Maier & Neustadt, L.L.P.

(57) ABSTRACT

An optical sensor (1) includes a sensor chip member (2) having an optical waveguide layer (21), a combination of an incidence end grating (22a) and an output end grating (22b) spaced from each other, in contact with the optical waveguide layer (21), and a reaction reagent (23) provided on the optical waveguide layer (21) to detect as an optical change a quantity of measurement object interposed between the incidence end grating (22a) and the output end grating (22b), and a chamber member (3) to have, when the sensor chip member (2) is assembled, a facing surface (F) in position facing the optical waveguide layer (21), and a gap (I) defined between the optical waveguide layer (21) and the facing surface (F), the reaction reagent (23) being disposed in the gap (I).

13 Claims, 5 Drawing Sheets

OPTICAL SENSOR

CROSS REFERENCE TO RELATED APPLICATIONS

This application is based upon and claims the benefit of priority from prior Japanese Patent Applications, No. 2007-289082 filed on Nov. 6, 2007, and No. 2008-272205 filed on Oct. 22, 2008, the entire contents of which are incorporated herein by reference.

BACKGROUND OF THE INVENTION

1. Field of the Invention

The present invention relates to an optical sensor to be used in detection of a chromogenic reaction of an object of measurement.

2. Description of the Related Art

As concentration measuring methods for measurement objects such as varieties of hormones, such as insulin, proteins, or glycemia, there can be taken the following methods as examples. For instance, among others, there is such a method that makes a measurement of a voltage developed in an electrode reaction, and an optical concentration measuring method that uses a pigment to be absorbed by reaction with a substance to measure its chromatic change in terms of a change in quantity of light such as laser light. Among those, the optical concentration measuring method is advantageous in that it provides a measurement with high degradation ability.

The optical concentration measuring method employs a sensor chip for holding a measurement object during a measurement, as well as for wave-guiding a beam of laser light. FIG. 8 is a simple illustration for explanation of an exemplary sensor chip. As illustrated in FIG. 8, the sensor chip 100 is configured with a glass chip 101 for wave-guiding a beam of laser light, a pair of gratings 102a and 102b provided on the glass chip 101 for changing directions of rays of laser light having income to the sensor chip 100, and a measuring region 103 for a measurement object S to be held thereon.

Brief description of the optical concentration measuring method follows. First, a liquid measurement object S is injected inside the measuring region 103, and for instance a pigment is reacted with the measurement object S for adaptation to absorb incident light in accordance with concentration of the measurement object S. After that, rays of laser light are guided inside the glass chip 101 as illustrated in FIG. 8, and those rays of laser light having come through the measuring region 103, where the measurement object S was injected, are taken outside the glass chip 101 to detect the light quantity. From a detected value of light quantity, a concentration of the measurement object S is estimated.

For measurements of concentration using the optical concentration measuring method, it is required to prevent a liquid measurement object from flowing on a glass chip or the like. Hence, the measurement object is dropped in a region opened simply at the upside like the measuring region 103 as illustrated in FIG. 8 for instance, where the measurement object is held for measurement.

Further, there has been disclosed also a method in which a specimen is brought into direct contract with a meshed conductive thin-film side of an optical waveguide type glucose sensor, while making the concentration measurement, like an invention described in Japanese Patent Application Laying-Open Publication No. 2004-212188. For this invention, for instance a pulsing electric field is applied to the specimen, to sample a biologic fluid containing glucose as a measurement object from the specimen.

SUMMARY OF THE INVENTION

However, such a measuring method as according to the invention disclosed in Japanese Patent Application Laying-Open Publication No. 2004-212188 needs a so-called fine invasive action to a specimen to obtain a measurement object. It thus has a side that they can't always refer to as a general concentration measuring method.

Further, also in more general methods that have a liquid measurement object disposed on a glass chip or the like to make a measurement, there is a difficulty observed in some cases to hold the liquid measurement object on a glass chip or the like during the measurement. For instance, if the glass chip and the measuring region are flat, it is difficult to hold thereon a liquid measurement object, whether the liquid quantity of measurement object is large or small.

On the other hand, even in the case in which a measurement object is dropped in a measuring region opened simply at the upside, and the measurement object is held therein for measurement, it is observed that a liquid surface of measurement object becomes convex or concave in the measuring region due to a surface tension between a dropped liquid and the wall. If a liquid measurement object thus has a convex or concave form in the measuring region, rays of laser light having income to a waveguide may go as scattered light or stray light, with some striking into a light receiver, constituting a difficulty to perform a measurement with a favorable precision.

Further, the quantity of measurement object to be dropped in the measuring region, if smaller than prescribed, may obstruct the measurement as will be later-described, and 100 μl or more of liquid may be required in most cases. In contrast, for some measurement objects, if valuable for instance, it may be difficult to have a large quantity of measurement object availed for measurement, and in some cases, it may be required to enable a measurement with a smaller quantity. And, for measurements using a small quantity of measurement object, as this has to have a low liquid surface even when dropped in a measuring region opened at the upside, rays of light from an air layer may be reflected, resulting in a failure to perform a measurement with a favorable precision, in some cases.

Additionally, for such a sensor chip as illustrated in FIG. 8, it is difficult to drop a measurement object in a prescribed measuring region, there being happened, among others, a failure to have measurement object successfully put in the measuring region, or a failure for droplets at some positions to spread as necessary over locations in the measuring region, which also constitutes a cause to invite a reduced precision of measurement.

SUMMARY OF THE INVENTION

According to a first aspect of the present invention, an optical sensor comprises a sensor chip member comprising an optical waveguide layer, a combination of an incidence end grating and an output end grating spaced from each other, in contact with the optical waveguide layer, and a reaction reagent configured on the optical waveguide layer to detect as an optical change a quantity of measurement object interposed between the incidence end grating and the output end grating, and a chamber member configured to have, when the sensor chip member is assembled thereto, a facing surface in position facing the optical waveguide layer, and a gap defined between the optical waveguide layer and the facing surface, the reaction reagent being disposed in the gap.

According to a second aspect of the present invention, an optical sensor comprises a sensor chip member comprising an optical waveguide layer, a combination of an incidence end grating and an output end grating spaced from each other, in contact with the optical waveguide layer, a reaction reagent configured on the optical waveguide layer to detect as an optical change a quantity of measurement object interposed between the incidence end grating and the output end grating, and a hydrophile absorption film configured on the reaction reagent to absorb the measurement object, and a chamber member configured to have, when the sensor chip member is assembled thereto, a facing surface in position facing the optical waveguide layer, and a gap defined between the optical waveguide layer and the facing surface, the reaction reagent being disposed in the gap.

According to a third aspect of the present invention, an optical sensor comprises a sensor chip member comprising an optical waveguide layer, a combination of an incidence end grating and an output end grating spaced from each other, in contact with the optical waveguide layer, and a reaction reagent configured on the optical waveguide layer to detect as an optical change a quantity of measurement object interposed between the incidence end grating and the output end grating, and a chamber member configured to have, when the sensor chip member is assembled thereto, a facing surface in position facing the optical waveguide layer, and a gap defined between the optical waveguide layer and the facing surface, the reaction reagent being disposed in the gap, the gap being formed with a distance to hold the measurement object between from a face of the optical waveguide layer of the sensor chip member to the facing surface of the chamber member.

According to a fourth aspect of the present invention, an optical sensor comprises a sensor chip member comprising an optical waveguide layer, a combination of an incidence end grating and an output end grating spaced from each other, in contact with the optical waveguide layer, and a reaction reagent configured on the optical waveguide layer to detect as an optical change a quantity of measurement object interposed between the incidence end grating and the output end grating, and a chamber member configured to have, when the sensor chip member is assembled thereto, a facing surface in position facing the optical waveguide layer, and a gap defined between the optical waveguide layer and the facing surface, the reaction reagent being disposed in the gap, the chamber member comprising an injection port configured to inject the measurement object to the gap.

DETAILED DESCRIPTION OF THE PREFERRED EMBODIMENTS

There will be described into details preferred embodiments of the present invention, with reference to the accompanying drawings.

First Embodiment

Description is now made of an optical sensor according to a first embodiment of the present invention. According to the embodiment, the optical sensor 1 is configured with a sensor chip member 2 adapted for a measuring light beam to pass therethrough for a measurement and provided with a measuring region, and a chamber member 3 configured to be assembled with the sensor chip member 2 for holding a measurement object to enable a higher precision of measurement.

Figure 1:
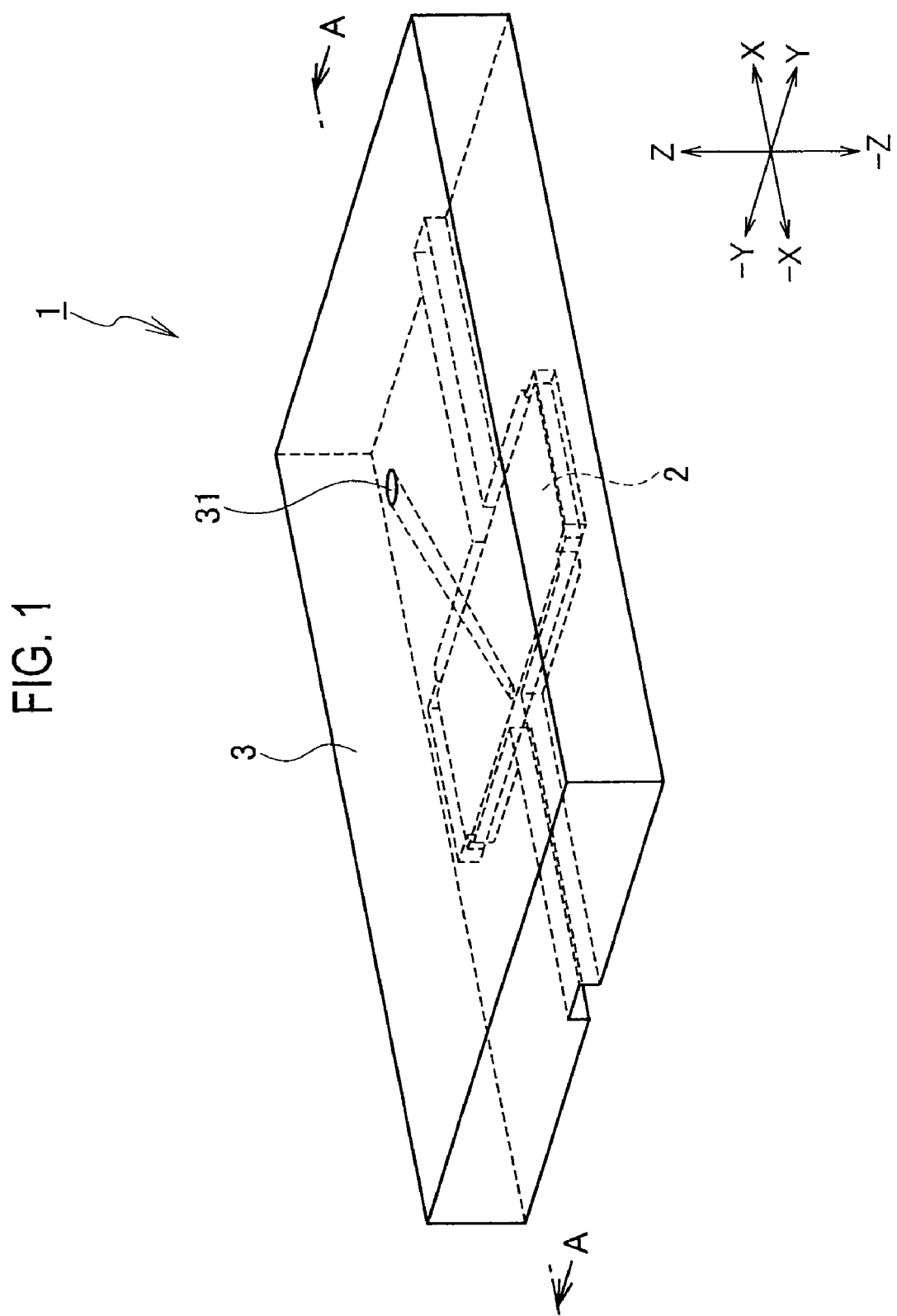
FIG. 1 is a perspective view of an entire configuration of an optical sensor according to a first embodiment of the present invention.
Figure 2:
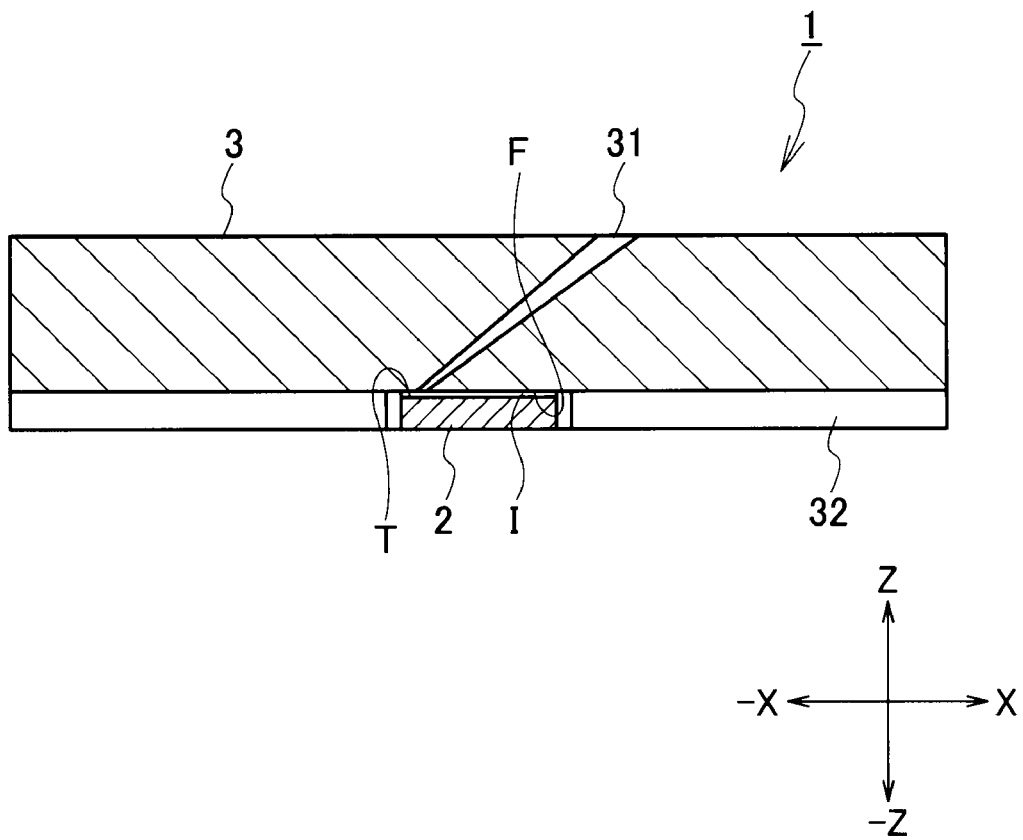
FIG. 2 is a sectional view of the optical sensor as cut along line A-A of FIG. 1.

The optical sensor 1 has such a configuration as illustrated by a perspective view in FIG. 1 for instance. The optical sensor 1 is composed of the sensor chip member 2 and the chamber member 3, as described. That is, the sensor chip member 2 has a face thereof for a reaction reagent to be put thereon (this face being referred herein to "upside T" of the sensor chip member 2), which faces the chamber member 3 when the sensor chip member 2 is fit therein, from a downside thereof, to thereby constitute the optical sensor 1. FIG. 2 is a sectional view of the optical sensor 1 as cut along line A-A of FIG. 1. It is noted that FIG. 1 and FIG. 2, depicting a configuration of the chamber member 3, provide a simple representation of the sensor chip member 2 that defines a mode of combination in between. The sensor chip member 2 is represented by broken lines in FIG. 1, and hatched lines in FIG. 2.

As illustrated in FIG. 1, the chamber member 3 has a substantially rectangular parallelepiped configuration. According to the first embodiment of the present invention, the chamber member 3 has, at a surface thereof opposing its top surface (which is the aspect to which the sensor chip member 2 is joined, this aspect being referred herein to "bottom aspect" for convenience) in the direction of Z axis, an injection port 31 formed therein for injecting a measurement object to a sensing film of the sensor chip member 2 as assembled. The injection port 31 is provided through the chamber member 3 as illustrated in FIG. 1, more specifically in FIG. 2, obliquely from a top aspect to the bottom aspect of the chamber member 3, extending in a direction from a +X side to a −X side.

This configuration is employed for enhancement of operability of a pipette, for instance, in use of the pipette for injecting a measurement object to the sensor chip member 2. That is, a person in charge of operation to inject a measurement object (referred herein sometimes to "operator" for convenience) is assumed as holding a pipette with the right hand to insert its distal end into the injection port 31 and inject the measurement object. In this situation, if the injection port 31 is provided upright, the right hand that holds the pipette has to be turned, so the measurement object is to be injected by an improper position. Resultant unsuccessful manipulation may cause the measurement object to be injected by an excessive amount than prescribed, or by a lacking amount, whichever gives rise to a reduced precision of measurement.

Therefore, the injection port 31 is configured to extend obliquely from top right to bottom left in FIG. 2, allowing for a pipette held with a right hand of an operator to be kept as it is in a proper position to inject a measurement object toward the sensor chip member 2.

It is noted that the injection port 31 of the chamber member 3, which is configured as described in the first embodiment, may be formed at another location on the top aspect of the chamber member 3 to permit the use irrespective of hand dominance of operator, or a plurality of injection ports 31 may well be formed.

The chamber member 3 is formed at the bottom aspect with a portion hollowed as a place for the sensor chip member 2 to be fit therein. To this portion, the upside T of the sensor chip member 2 is fit inwardly of the chamber member 3. In the embodiment of the present invention, the sensor chip member 2 is fit in the chamber member 3, with such a positional relationship that a short side of the sensor chip member 2 is parallel to a long side of the chamber member 3. However, it can be set arbitrarily in which positional relationship the sensor chip member 2 is to be fit in the chamber member 3. Further, for the sensor chip member 2 to be kept from falling off the chamber member 3, there may be used an adhesive or the like, or the sensor chip member 2 may be held by the chamber member 3 itself, as it is fit in the bottom aspect of the chamber member 3.

Further, the chamber member 3 has at the bottom aspect a discharge vent 32 formed therein for relieving pressures developed as the sensor chip member 2 is fit and a measurement object is injected. According to the first embodiment, as illustrated in FIG. 1 and FIG. 2, the discharge vent 32 is formed in a central part of the chamber member 3 in the direction of Y axis, and over length of the long side in the direction of X axis, in consideration of positional relationships with the sensor chip member 2 to be fit. However, the discharge vent 32 may well be provided in any part of the chamber member 3, so far as it can relieve pressures. The discharge vent 32 is adapted to vent, besides pressures described, gases, liquids, and the like that reside between the sensor chip member 2 and the chamber member 3.

The chamber member 3 may be acrylic for instance. And, the chamber member 3 is colored black at least within a region of a surface in position facing the upside T of the sensor chip member 2 (this surface being referred herein to "facing surface F" of the chamber member 3). Or otherwise, an entirety of the chamber member 3 may be made of a black material. The chamber member 3 employs for instance a black as its color. If the chamber member 3 were made of a transparent acrylic resin, rays of light in a laser shot from a measuring device for detecting a reaction (referred herein simply to "measuring device") would have been scattered or strayed upon incidence on an optical waveguide of the sensor chip member 2, failing to implement a high precision of measurement. The chamber member 3 rendered black affords scattered light and stray light to be reduced, contributing to an enhancement of measurement precision.

In addition, the facing surface F is processed for hydrophilization of its region to enable an even and quick spread of measurement object over the measuring region, allowing for a high precision of measurement. Typically, contact angles of 65° or less provide a hydrophilia. For this, over the region of facing surface F, a hydrophilization process may be implemented by performing for instance a wetting process using an acid or alkali, a drying process using UV rays or ozone, and an application process using a hydrophile coating agent. Or, there may be implemented a hydrophilization process such as by use of a method of gluing on the facing surface F at least one of a hydrophile film and a film hydrophilized as described above (this may encompass using such a film that has a non-hydrophile nature and is hydrophilization-processed as described above).

Figure 3:
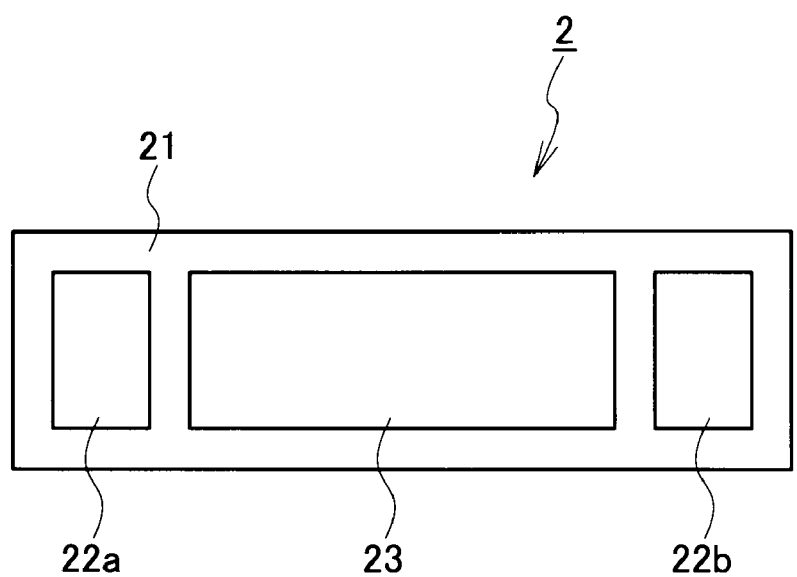
FIG. 3 is a plan view of a sensor chip according to the embodiment of the present invention.

FIG. 3 is a plan view for illustration in which an upside of the sensor chip member 2 is seen. This plan view shows an optical waveguide layer 21, a combination of an incidence end grating 22a and an output end grating 22b spaced from each other, in contact with the optical waveguide layer 21, and a reaction reagent 23 provided for detecting as an optical change a quantity of measurement object interposed between the incidence end grating 22a and the output end grating 22b, in contact with the optical waveguide layer 21.

The optical waveguide layer 21 is a layer adapted as a passage for rays of light in a laser shot from the measuring device. For the optical waveguide layer 21, it is favorable to use, among others, an alkali-free glass or an organic resin for instance (e.g. a thermosetting resin such as an epoxy resin). Rays of laser light having passed the optical waveguide layer 21 have their directions changed by the output end grating 22b, and outgo again from the optical waveguide layer 21 to enter a light receiving means in the measuring device. For an optical concentration measuring method, rays of laser light passing the optical waveguide layer 21 as described pass a region for placement of the reaction reagent 23 to be described later (this region being referred herein sometimes to "sensing region"), whereby laser light has a reduced intensity, which is measured to thereby implement the method of measuring a concentration of measurement object.

The incidence end grating 22a and the output end grating 22b (referred herein sometimes collectively to "grating 22") are configured to change directions of rays of light in a shot laser. The grating 22 contacting the optical waveguide layer 21 may be made of titanium oxide for instance, with a cover of thermosetting resin thereover. The grating 22 may be made also of a material properly selected from among tin oxide, zinc oxide, lithium niobate, gallium arsenide (GaAs), indium tin oxide (ITO), polyimide, and the like, besides titanium oxide. The incidence end grating 22a and the output end grating 22b are spaced from each other, to be formed with the sensing area in between. It is noted that in FIG. 3 one of the two is provided as an incidence end grating 22a, and the other, as an output end grating 22b, which however is a matter of convenience, and whichever may be an incidence end grating 22a or an output end grating 22b.

The incidence end grating 22a and the output end grating 22b have a sensing area in between, as described. The sensing area is provided with a reaction reagent 23, for an optical detection of reaction between an injected measurement object and the reaction reagent 23, to thereby implement a measurement of concentration of the measurement object. As a reaction between measurement object and reaction reagent 23, such a reaction can be taken as a chromogenic, luminescent, absorption, scattering, refractive-index change, or fluorescent.

Description is now made of the embodiment of the present invention, for an example using a reaction reagent to develop a chromogenic reaction. The reaction reagent 23 may be provided as it is on the sensor chip member 2, or may be accommodated in a holder for holding the reaction reagent 23, to provide on the sensor chip member 2. Here, description is made of an example using a film as the holder for holding the reaction reagent 23. For a convenient description, such an entirety that includes a reaction reagent 23 and a film-shape holder will be referred to as a "sensing film 23".

A liquid measurement object is injected to the sensing film 23, whereby the sensing film 23 is soaked with the measurement object. The sensing film 23 may be formed by using, for instance, oxidase (GOD), peroxidase (POD), 3,3',5,5'-tetramethylbenzidine (TMBZ), and hydroxyethyl cellulose (HEC) as a binder. It is noted that the sensing film 23 may be sized to any area so far as it is put in the sensing area.

Figure 4:
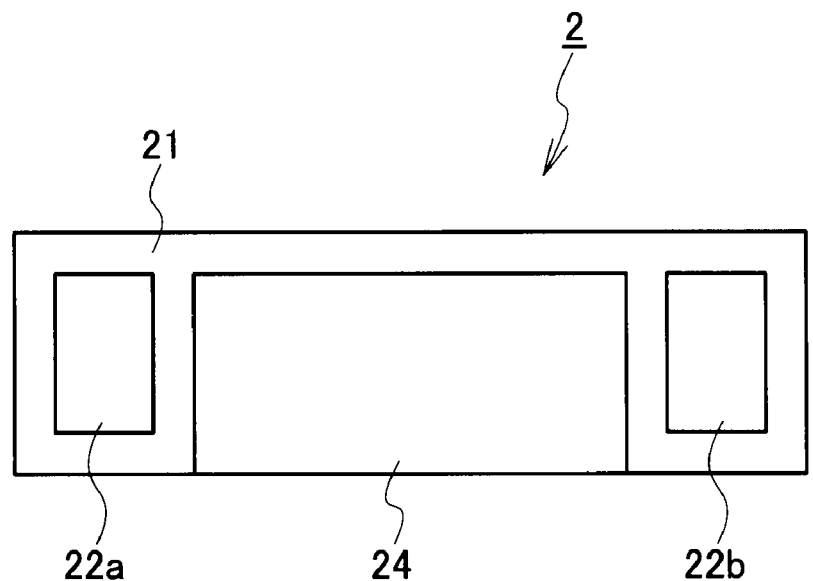
FIG. 4 is a plan view of the sensor chip according to the embodiment of the present invention.

According to the first embodiment, as illustrated in FIG. 4, the sensor chip member 2 further has a hydrophile film 24 disposed so as to cover substantially an entire region of the sensing film 23. The hydrophile film 24 may be any material so far as it can hold a measurement object injected through the injection port 31 of the chamber member 3, like a mesh for instance. Further, it varies which region of the sensing film 23 is covered with the hydrophile film 24, depending on a variety of factors, such as by how much quantity the measurement object is to be held in the sensing area. Accordingly, the region of layout can be set in an arbitrary manner.

However, it per se also is arbitrary whether or not the hydrophile film 24 is to be disposed on the sensing film 23. That is, for example, for a sensing film 23 having a hydrophobic nature, even if a measurement object is injected on the sensing film 23, the liquid will be shed, containing gaseous bodies. Under this condition, even if a measurement is made, it suffers from a difficulty to hold the measurement object on the sensing area, and one can't ask for a high precision of measurement. Hence, in such a case, a hydrophile film 24 is placed on the sensing film 23, to thereby facilitate holding a measurement object on the sensing area. On the other hand, for a sensing film 23 having a hydrophile nature, it is easy to hold a measurement object on the sensing area, and in some cases, it can do without provision of a hydrophile film 24.

Figure 5:
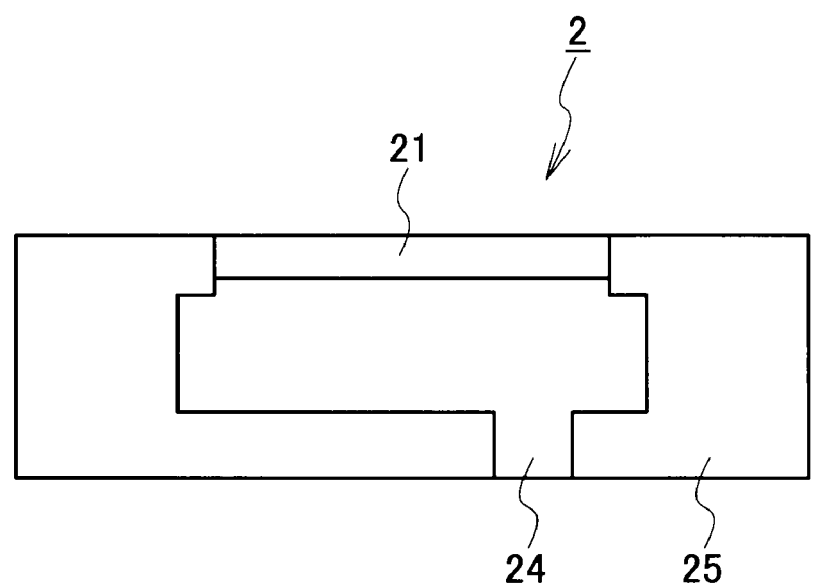
FIG. 5 is a plan view of the sensor chip according to the embodiment of the present invention.

Further, as illustrated in FIG. 5, there is a light shielding means 25 provided on the hydrophile film 24. By provision of the light shielding means 25, rays of laser light incoming from the measuring device are kept from getting scattered or strayed with a reduced precision of measurement. According to the embodiment of the present invention, the sensor chip member 2 may have a light shielding tape with an excellent light-shielding property for instance employed as a light shielding means 25 and patched mainly over regions of grating 22. To this point, at least a region of incidence end grating 22a may well be shielded in view of the aim of provision of light shielding means 25. It is noted that the light shielding means 25 may be used as a joint when the sensor chip member 2 is fit in the chamber member 3, thereby permitting the sensor chip member 2 to be prevented from falling off the chamber member 3. For example, for a light shielding means 25 being a double-faced black tape, it is possible to implement shielding laser light, while having the sensor chip member 2 and the chamber member 3 joined together to fix.

Description is now made of how to fit the sensor chip member 2 in the chamber member 3 and hold a measurement object in the optical sensor 1.

According to the first embodiment of the present invention, the optical sensor 1 is made up by fitting the sensor chip member 2 to the bottom aspect of the chamber member 3, as illustrated in FIG. 1 and FIG. 2. The sensor chip member 2 has a face (as the upside T) provided with the grating 22, sensing film 23, and hydrophile film 24, which is pressed into the chamber member 3 to thereby fit the sensor chip member 2.

Therefore, a face of the sensor chip member 2 opposing the upside (this face being referred herein to "downside" of the sensor chip member 2) is positioned on the same side as the bottom aspect of the chamber member 3. It is noted that in the optical sensor 1 according to the embodiment of the present invention, the downside of the sensor chip member 2 and the bottom aspect of the chamber member 3 are fit up to be flush, as illustrated in FIG. 2, whereas the sensor chip member 2 may be fit in the chamber member 3 so that the downside of the sensor chip member 2 and the bottom aspect of the chamber member 3 are not flush to each other.

When the sensor chip member 2 is fit in the chamber member 3, due to a relationship with a recess provided for the sensor chip member 2 to be fit therein, there is a gap I defined between the upside of the sensor chip member 2 and a surface (as the facing surface F) facing the upside T of the sensor chip member 2 inside the chamber member 3. This region of gap I thuds defined is communicating with the injection port 31 of the chamber member 3, and when a measurement object is injected from the injection port 31, the measurement object is put in the gap I.

The measurement object injected in the gap I as a very narrow space is held by the surface tension between the upside T of the sensor chip member 2 and the facing surface F, while being influenced also by, among others, a property of the injected measurement object and presence of the hydrophile film 24 described.

For the gap I, the facing surface F residing inside the chamber member 3 is off at a distance from the optical waveguide layer 21 of the sensor chip member 2, which may be determined in an arbitrary manner in consideration of a variety of factors such as the amount of injection of measurement object. That is, for the measurement object being held by the surface tension between the upside T of the sensor chip member 2 and the facing surface F, it can do with a distance that permits the measurement object to be kept held in the gap I. It is noted that in experiments by the inventor, measurements were made of a measurement object in a gap I with a 0.1 mm distance. As result of that, even after a plurality of measurements, the measurement results showed a small variation with a high precision of measurement.

In addition, for the gap I that has a smaller volume with a shorter distance between the upside T of the sensor chip member 2 and the facing surface F, the shorter this distance becomes the more it contributes to a quantity reduction of measurement object. Further, providing a secured high precision of measurement, the gap I for measurement object to be injected therein may well be rendered very small, with the upside T of the sensor chip member 2 brought into contact with the facing surface F.

With a reaction reagent reacting with a measurement object, a chromogenic reaction occurs on the sensing film 23 described. For measurement of a post-coloring light intensity at the sensing film 23, a laser beam or the like is radiated from the measuring device toward the incidence end grating 22a of the sensor chip member 2, and reflected light from the incidence end grating 22a is received by a light receiving element of the measuring device. The post-coloring light intensity thus measured has a difference to a reference light intensity measured in advance, whereby a concentration of the measurement object is estimated.

As a reaction between measurement object and reaction reagent 23, such a reaction can be taken as a luminescent, absorption, scattering, refractive-index change, or fluorescent, besides the chromogenic reaction, as described. According to the embodiment of the present invention, the optical sensor is applicable to any reaction. Description will be made of those reactions as well.

As for luminescent reaction, a concentration of measurement object is measured by measuring a luminescent reaction. As the method, the following two types of method can be taken for instance. The first luminescent reaction is a reaction in which, by a catalytic action of the GOD described, glucose is changed to a gluconic acid and a hydrogen peroxide solution, which is changed, by a catalytic action of POD added to the hydrogen peroxide solution, to an aminophthalic acid, emitting light. The intensity of this luminescence depends on the hydrogen peroxide solution, i.e., concentration of glucose, and a concentration of measurement object can be measured by measuring the luminescent intensity.

The second luminescent reaction employs an antigen-antibody reaction. An antibody is fixed to the sensor chip member, and an antigen is reacted with the antibody, and in addition an antibody labeled with POD is reacted. After that, it is washed to separate unreacted materials. And, with reacted materials left as not being separated, luminol and hydrogen peroxide water are reacted, whereby luminol becomes luminous in dependence on a quantity of antigen. By measuring this luminescent intensity, a concentration of measurement object can be measured.

The absorption reaction is a reaction to be caused by an absorption of laser light or the like radiated from the measuring device, as it is performed by reaction products produced by the reaction reagent in the chromogenic reaction described. Absorbed light by reaction products is received by the light receiving element of the measuring device, and its light intensity is measured. From a difference between this light intensity and the above-noted reference light intensity, a concentration of measurement object is measured.

The scattering and refractive-index change reactions are reactions that make use of precipitates to be produced by a reaction of the reaction reagent with a measurement object, or precipitates to be produced, after a reaction (e.g. a primary reaction) once made between the reaction reagent and the measurement object, by an additional reaction (e.g. any of secondary and subsequent reactions). That is, if precipitates are produced in any reaction, rays of light incoming from the measuring device strike on such precipitates, and are scattered, or have changed refractive indices. Such a scattering or refractive-index change is captured to thereby estimate a concentration of measurement object.

The fluorescent reaction employs the antigen-antibody reaction described. An antibody is fixed to the sensor chip member, and an antigen is reacted with the antibody, and further an antibody labeled with a fluorescent material is reacted. Then, the fluorescent material causes a fluorescent reaction in dependence on a quantity of antigen. By measuring this fluorescent intensity, a concentration of measurement object can be measured. It is noted that as examples of fluorescent material, there can be taken, among others, GDP (green fluorescent protein), Allophycocyanin and the like for instance.

Such being the case, a liquid measurement object is injected (to a gap) between mutually facing surfaces (an upside of a sensor chip member and a facing surface of a chamber member facing the upside), and the measurement object is held in the region by surface tension between the two surfaces and the measurement object, thereby allowing for a normal presence of measurement object on a reaction regent provided in a flat form on the sensor chip member.

Further, with a sensing film as a hydrophile material, or by use of a hydrophile film, the measurement object can be held, while being evenly and quickly spread over a sensing area, which affords provision of an optical sensor enabling the use of measurement object to be controlled to a small quantity, allowing for a higher precision of measurement than ever.

Further, with the chamber member rendered black, or by use of a light shielding means, influences by other light than sensing light are possibly eliminated, which also contributes to provision of an optical sensor allowing for a high precision of measurement.

For the present embodiment, it also is possible to supply a liquid measurement object from a substantially normal direction to the gap between the sensor chip member 2 and the chamber member 3, for a concentration measurement of measurement object to be performed in a similar manner to the above. In this case, the chamber member 3 to be employed may be configured with an injection port 31 substantially vertically provided through the member from the top aspect to the bottom aspect, to implement a concentration measurement of measurement object.

Second Embodiment

Description is now made of a second embodiment of the present invention. It is noted that in the second embodiment, like components to those components described in the foregoing first embodiment are designated by like reference characters, eliminating redundant description of identical components.

Figure 6:
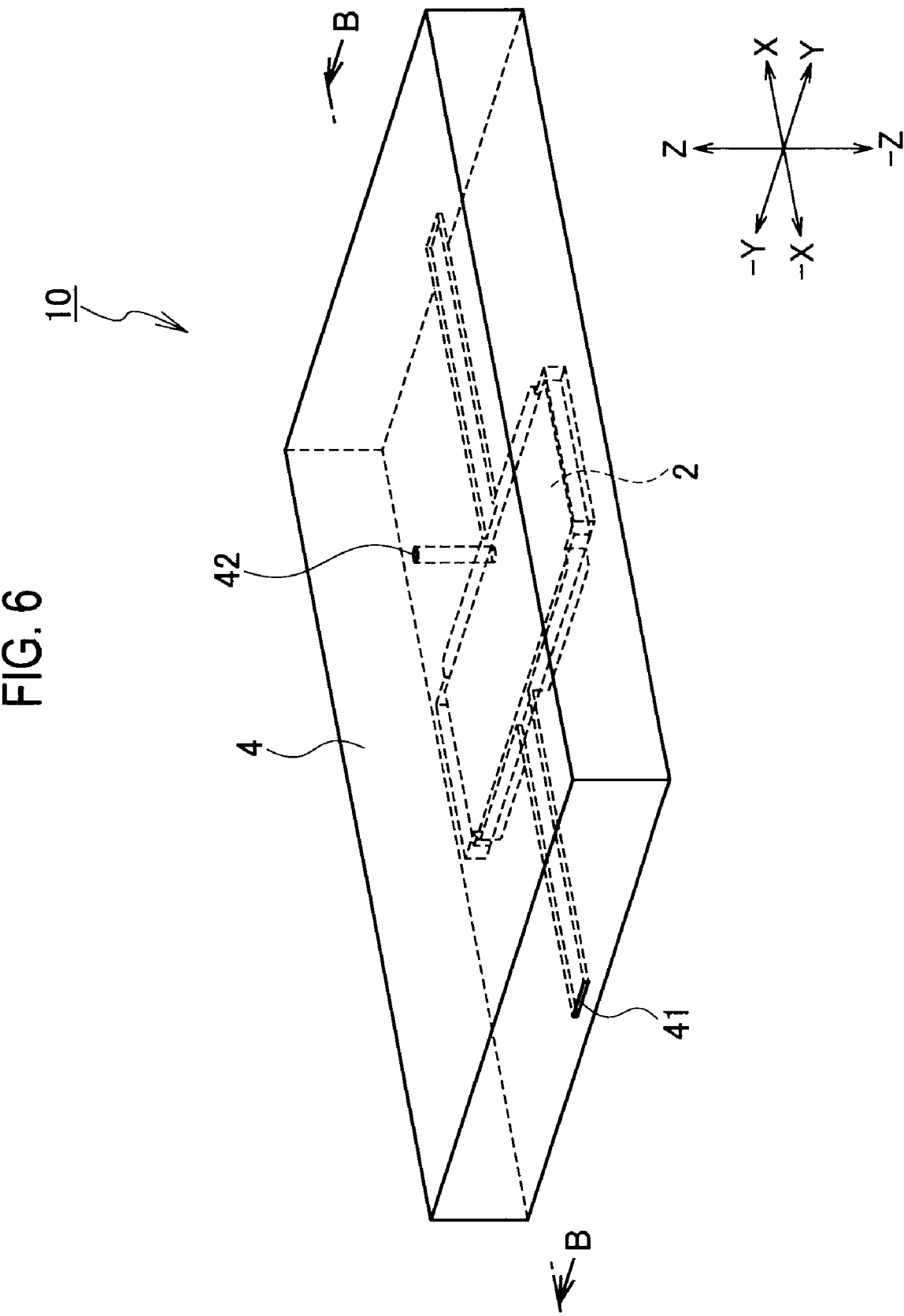
FIG. 6 is a perspective view of an entire configuration of an optical sensor according to a second embodiment of the present invention.
Figure 7:
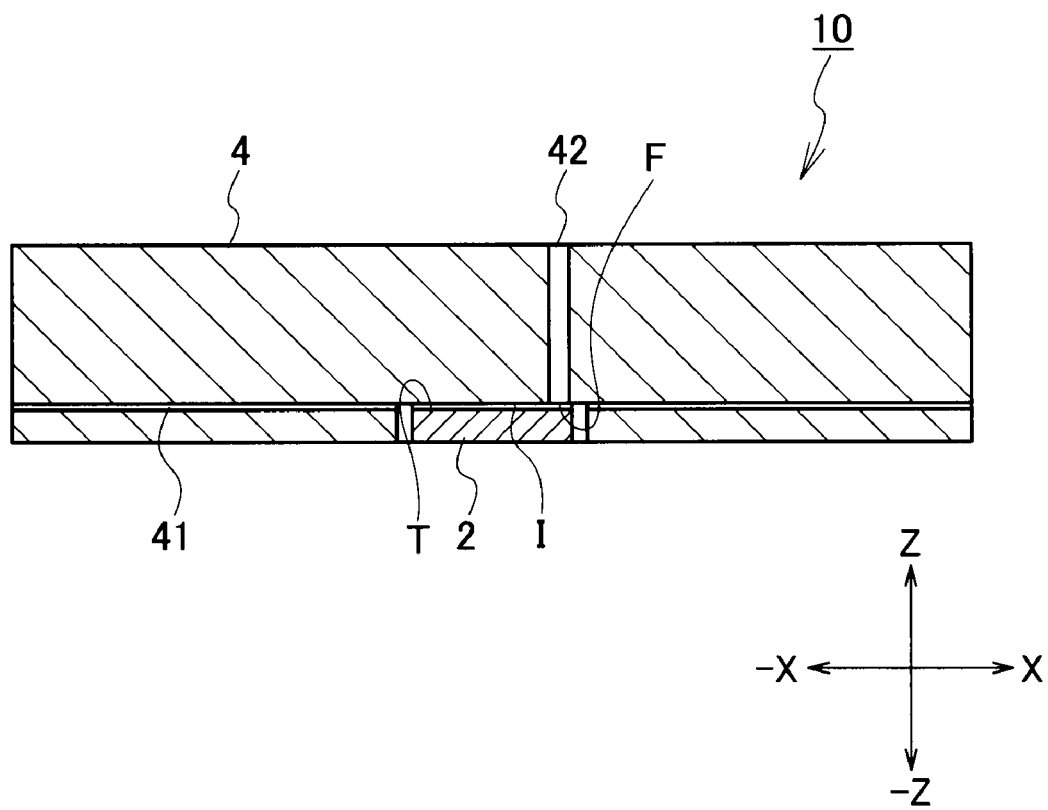
FIG. 7 is a sectional view of the optical sensor as cut along line B-B of FIG. 6.
Figure 8:
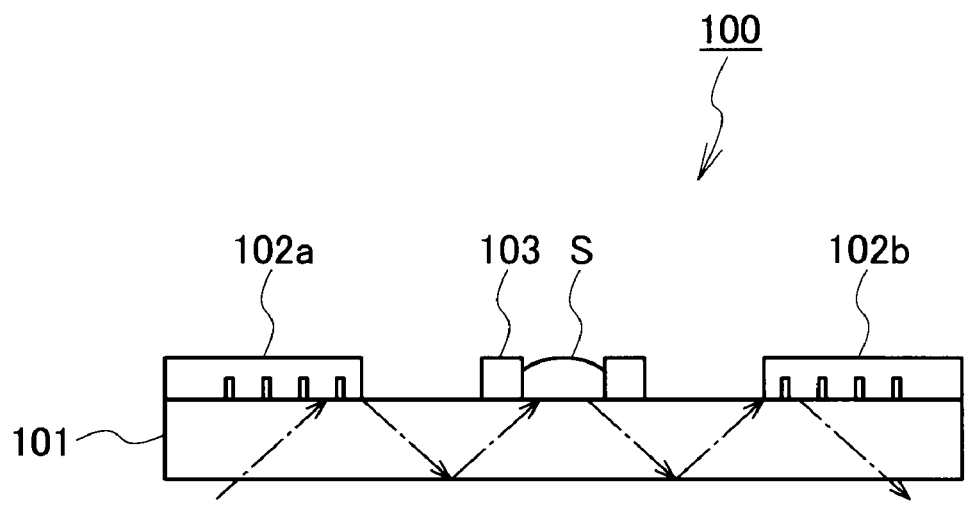
FIG. 8 is a sectional view of an optical sensor as a conventional example.

In the second embodiment, an injection port and a discharge vent provided in a chamber member are different in configuration and position, relative to the injection port 31 and the discharge vent 32 of the chamber member 3 in the first embodiment. That is, for the second embodiment, as illustrated in FIG. 6 and FIG. 7 as a sectional view along line B-B thereof, a chamber member 4 constituting an optical sensor 10 has an injection port 41 configured to inject a measurement object in an X-axis direction or –X-axis direction relative to a gap I defined by and between the chamber member 4 and a sensor chip member 2 fit therein, such that the injection port 41 pieces the chamber member 4 in the X-axis direction.

Such the configuration of injection port 41 permits an injection of measurement object to a sensing area by use of a pump or the like for instance, not an injection of measurement object by a pipette of an operator for instance.

Further, there is a discharge vent 42 oriented from the gap I to a top aspect of the chamber member 4. As described in the first embodiment also, the discharge vent 42 may be provided in an arbitrary portion of the chamber member 4, while it is provided in position illustrated in FIG. 6 and FIG. 7 in consideration of an easy processing or the like, for the second embodiment in which the injection port 41 is provided in the above-noted position.

Such the positioning of injection port 41 and discharge vent 42 provides use of the optical sensor 10 with new effects, such as a possible automatic injection of measurement object for instance.

Other points of configuration are identical to the optical sensor according to the first embodiment, and it is possible to provide an optical sensor adapted for a reduction in quantity of measurement object in use, as well as an even and quick spread of the measurement object to be held as it is on a measuring region of a sensor chip member being flat, permitting a possible elimination of influences by other light else than sensing light, allowing for a high precision of measurement. Further, with the chamber member rendered black, or by use of a light shielding means, influences by other light than sensing light are possibly eliminated, which also contributes to provision of an optical sensor allowing for a high precision of measurement.

Further, this invention is not restricted to the foregoing embodiments, and in a practical stage it may be implemented by modifications of components within a range not departing from the drift. In addition, a plurality of components disclosed in the foregoing embodiments may be adequately combined to devise a variety of inventions. For instance, among the whole components disclosed in the embodiments, some components may be omitted. Further, between different embodiments, associated components may be adequately combined.

What is claimed is:

1. An optical sensor comprising:
a sensor chip member comprising an optical waveguide layer, a combination of an incidence end grating and an output end grating spaced from each other, in contact with the optical waveguide layer, a sensing region interposed between the incidence end grating and the output end grating, and a reaction reagent configured on a surface of the sensing region to detect as an optical change a quantity of measurement object; and
a chamber member configured to have, when the sensor chip member is assembled thereto, a facing surface facing the sensing region, and a void defined between the reaction reagent surface of the sensing region and the facing surface.

2. The optical sensor according to claim 1, wherein the optical change comprises one of a chromogenic, a luminescent, an absorption, a scattering, and a refractive-index change.

3. The optical sensor according to claim 1, wherein the optical change is caused by a fluorescent reaction.

4. An optical sensor comprising:
a sensor chip member comprising an optical waveguide layer, a combination of an incidence end grating and an output end grating spaced from each other, in contact with the optical waveguide layer, a reaction reagent configured on the optical waveguide layer to detect as an optical change a quantity of measurement object interposed between the incidence end grating and the output end grating, and a hydrophile absorption film configured on the reaction reagent to absorb the measurement object; and
a chamber member configured to have, when the sensor chip member is assembled thereto, a facing surface in position facing the optical waveguide layer, and a gap defined between the optical waveguide layer and the facing surface,
the reaction reagent being disposed in the gap.

5. The optical sensor according to claim 4, wherein the sensor chip member comprises a light shielding means covering a region including at least one of the incidence end grating and the output end grating as a surface of the optical waveguide layer.

6. The optical sensor according to claim 5, wherein the light shielding means is black.

7. The optical sensor according to claim 6, wherein the light shielding means comprises a joint material for the sensor chip member and the chamber member to be joined to fix.

8. An optical sensor comprising:
a sensor chip member comprising an optical waveguide layer, a combination of an incidence end grating and an output end grating spaced from each other, in contact with the optical waveguide layer, a sensing region interposed between the incidence end grating and the output end grating and a reaction reagent configured on a surface of the sensing region to detect as an optical change a quantity of measurement object; and
a chamber member configured to have, when the sensor chip member is assembled thereto, a facing surface facing the sensing region, and a void defined between the reaction reagent surface of the sensing region and the facing surface,
the void being formed to hold the measurement object therein.

9. The optical sensor according to claim 8, wherein the facing surface of the chamber member defining the void is hydrophilization-processed.

10. An optical sensor comprising:
a sensor chip member comprising an optical waveguide layer, a combination of an incidence end grating and an output end grating spaced from each other, in contact with the optical waveguide layer, and a reaction reagent configured on the optical waveguide layer to detect as an optical change a quantity of measurement object interposed between the incidence end grating and the output end grating; and
a chamber member configured to have, when the sensor chip member is assembled thereto, a facing surface in position facing the optical waveguide layer, and a gap defined between the optical waveguide layer and the facing surface,
the reaction reagent being disposed in the gap,
the chamber member comprising an injection port configured to inject the measurement object to the gap.

11. The optical sensor according to claim 10, wherein the chamber member comprises a discharge vent configured to relieve pressures from the gap when the measurement object is injected.

12. The optical sensor according to claim 10, wherein the chamber member is rendered black at least in a region of the facing surface defining the gap.

13. The optical sensor according to claim 11, wherein the chamber member is rendered black at least in a region of the facing surface defining the gap.

* * * * *